United States Patent [19]

Gilvarg et al.

[11] 4,454,065

[45] Jun. 12, 1984

[54] OLIGOPEPTIDE PRODRUGS

[75] Inventors: Charles Gilvarg, Princeton, N.J.; William D. Kingsbury, King of Prussia, Pa.

[73] Assignee: SmithKline Beckman Corporation, Philadelphia, Pa.

[21] Appl. No.: 507,326

[22] Filed: Jun. 23, 1983

Related U.S. Application Data

[63] Continuation-in-part of Ser. No. 379,537, May 18, 1982, abandoned.

[30]    Foreign Application Priority Data

Apr. 22, 1983 [ZA]  South Africa .................. 83/2844

[51] Int. Cl.$^3$ ............................................. C07C 103/52
[52] U.S. Cl. ............................................. 260/112.5 R
[58] Field of Search ................................. 260/112.5 R

[56]            References Cited

U.S. PATENT DOCUMENTS

| | | | |
|---|---|---|---|
| 4,087,520 | 5/1978 | Braun et al. | 260/112.5 R |
| 4,169,141 | 9/1979 | Topliss et al. | 260/112.5 R |
| 4,215,112 | 7/1980 | Goldstein et al. | 260/112.5 R |
| 4,264,590 | 4/1981 | Chu et al. | 260/112.5 R |
| 4,302,386 | 11/1981 | Stevens | 260/112.5 R |
| 4,309,342 | 1/1982 | Chu et al. | 260/112.5 R |

FOREIGN PATENT DOCUMENTS

| | | |
|---|---|---|
| 0038541 | 10/1981 | European Pat. Off. . |
| 2553689 | 10/1976 | Fed. Rep. of Germany . |
| 53-3007619 | 1/1978 | Japan . |
| 54-4048773 | 4/1979 | Japan . |
| WO81/01290 | 4/1981 | PCT Int'l Appl. . |

OTHER PUBLICATIONS

T. E. Fickel, et al., Nature, The New Biology, 241, 161, 1973.
Ponpipom, et al., J. Med. Chem., 24, 1388, (1981).
B. N. Ames, Proc. Nat. Acad. Sci., OSH 70, 456, (1973).
B. Ishai, Tetrahedron, (1976), 1571.
T. Nishitani, et al., J. Org. Chem., 44, 2019, (1979).
T. Iwasaki, et al., J. Org. Chem., 12, 2419, (1977).
T. Nishitani, et al., Chem. Pharm. Bull., 28, 1137, 1980.
R. K. Olsen, et al., Tetrahedron Letters, 41, 3579, (1975).

*Primary Examiner*—Delbert R. Phillips
*Attorney, Agent, or Firm*—William H. Edgerton; Richard D. Foggio; Alan D. Lourie

[57]            ABSTRACT

Prodrugs are described whose structures have a oligopeptide chain which is substituted by a nucleophilic chemotherapeutic residue at the α-position. The products have increased cell membrane permeability and beneficial physico-chemical properties.

10 Claims, No Drawings

OLIGOPEPTIDE PRODRUGS

This application is a continuation-in-part of U.S. patent application Ser. No. 379,537 filed May 18, 1982, now abandoned.

This invention relates to oligopeptide containing prodrugs of selected chemical compounds which are useful in the pharmaceutical art and to chemical intermediates or methods for preparing such prodrugs. The compounds are useful in a method for transporting impermeant chemotherapeutic agents through the cell membranes of infecting species, then, releasing the active agents intracellularly. Others, as pointed out hereafter, are also useful to prepare useful product forms or as enzyme substrates used for assaying enzyme content in biological fluids.

GENERAL BACKGROUND OF THE INVENTION

The prior art recognizes that peptide transport systems are one mechanism by which chemical substances are carried into the cell membrane of an infecting organism. It has been postulated that both dipeptide and oligopeptide transport systems are present in the cell membrane, for example, in the cell membrane of *Escherichia coli;* B. N. Ames, Proc. Nat. Acad. Sci. OSH 70 456 (1973) or C. Gilvarg, Nature, the New Biology 241 161 (1973). The dipeptide transport system is more specific in its ability to transport than is the oligopeptide transport system.

Peptide transport systems are widespread in both procaryotic and eukaryotic microorganisms. A prodrug which can be transported per se through the cell membrane of infecting organisms via such a permease system and, then, releases the drug within the cell would possess enhanced activity.

A number of synthetic derivatives have been prepared to take advantage of this transport system such as those described by M. M. Ponpipom, et al., J. Med. Chem. 24 1388 (1981), European Patent Office application 38,541 or C. Philip, et al., PCT application, W081/01145. Some of these types of compounds were designed to limit toxicity or to achieve more specific biological activity. Such compounds of the prior art either are limited in scope or are aimed at being biologically active without degradation at the receptor site, that is, in the transport form, due to their resistance to intracellular peptidases. For example, the cited Philip publication discloses anti-tumor moieties which are covalently attached to a polypeptide. A covalently bound group must be active per se. This differs from the present invention in which the warhead or biologically active group is reversibly attached.

A number of potentially useful chemotherapeutic agents are present in the prior art which are impermeant or poorly permeant to the cell membrane of an infecting organism. The impermeant nature of these compounds may be either due to the inherent physico-chemical properties of the compounds or due to an acquired resistance to the drug by the permease system of the cell membrane of the target species.

CHEMICAL BACKGROUND OF THE ART

B. Ishai, Tetrahedron (1976) 1571 or Technion, German Pat. No. 2,553,689 (Farmdoc 46408X) discloses the reaction of glyoxylic acid and a primary amide to form an α-hydroxyamino acid. It does not disclose the reaction of glyoxylic acid with an amino acid amide to form a peptide which has a hydroxy substituent at the α-carbon as described hereafter.

Publications, such as Japanese Pat. Nos. 54,048,773 (Farmdoc 41180B/22) and 53,007,619 [as well as the scientific publications corresponding to these patents, T. Nishitani, et al., J. Org. Chem. 44 2019 (1979); T. Iwasaki, et al., J. Org. Chem. 12 2419 (1977); T. Nishitani, et al., Chem. Pharm. Bull. 28 1137 (1980)] together with R. K. Olsen, et al., Tetrahedron Letters, 41 3579 (1975), describe the preparation of certain α-acetoxy amino acids and displacement of the α-acetoxy group by displacing radicals, including 5-fluorouracil or mercaptans. No peptides, which are reversibly α-substituted, are described in the prior art to the best of our knowledge.

DESCRIPTION OF THE INVENTION

The structures of the prodrugs of this invention have been found to have a number of requirements necessary for acceptance by the receptors of the permease system in the cell membrane of the infecting organism and by the intracellular peptidases. These respective receptor systems are necessary, first for transport and, then, for release of the active drug within the cell of the infecting or toxic species.

The compounds of this invention have an oligopeptide chain in which an active moiety is reversibly substituted at the α-position of a glycyl unit which, in turn, must be attached, for stabilization, to a residue of the oligopeptide chain by means of the amino group of the glycyl carrying unit.

It should be noted that, in the disclosure of this invention, the glycyl carrying unit is called the 1 unit, the stabilizing unit adjacent is called the 2 unit. The carboxy or C— end of the chain is represented by Q in the structures of formula I hereinafter, the amino or N— end as P. Also, one skilled in the art, reading this disclosure, will recognize that the carrying unit may be at any position of the oligopeptide unit as long as a stabilizing amino acid is adjacent to said glycyl unit. For convenience of synthesis, the carrying unit is usually, and preferably, represented, herein and in the claims, as the carboxy terminal unit of the chain.

Therefore, oligopeptide chain will usually have a free carboxy group at the carboxy terminal or the 1 unit, the unit to which the drug or warhead is attached, or must be able to generate such a carboxy unit in vivo. It must, even more critically, have a free amino group at the N-terminal amino acid unit or must be able to generate such a unit in vivo. Each amino acid unit, other than the carrying unit, is, preferably, in its natural form. All the chemical protective groups necessary during the preparation of the prodrugs are removed unless they are removed in situ in the biological system in which the end products of this invention are to be used or serve a purpose without removal such as with certain enzyme substrates described hereinafter.

Finally, the stereoisomeric configuration of the carrying amino acid unit must be L. The D-form has been found, to date, not to transport. The first two units of the polypeptide chain are preferably L in configuration. These units are the carrying unit (1 unit) and the amino containing (2 unit). The remaining units of the polypeptide chain are less critical and may be either D or L, or a mixture of configurations. Preferably, however, the amino acid units are all L and, for ease of preparation, all the same at the 3–6 units in either direction along the peptide chain. It has been found in the dipeptide series that, when the configuration of the respective 1-2 units are L-L, L-DL or DL-DL, only the L-L form of the D-containing mixtures is transported, the compound having a D-terminal unit is left behind. The two L-units of the oligopeptide at the 1 and 2 positions have, furthermore, been found to stabilize the prodrug to spontaneous decomposition.

Since the 1 unit should be L, it must be α- or 2-substituted, at least by the "warhead" residue, that is, by the residue which is useful as described hereafter. Such α-substitution, also, is important, not only to formation of the prodrug by a nucleophilic substitution reaction, but to release the active groups or warhead within the cells of the infecting organism. Intracellular peptidases split the polypeptide unit between the 1 and 2 units within the cell. The active drug is, then, released from the sole amino acid residue remaining by spontaneous decomposition of the unit which no longer possesses the stabilizing amino acid units of the chain. In vitro evidence is presented in the utility example to support this mechanism of action. The splitting of the peptide chain is also important when the compounds of this invention are used as enzyme substrates in analytical procedures.

In this disclosure, the term, oligopeptide, is used to describe the carrying tail(s) of the prodrug but includes both dipeptide or higher oligopeptide chains. L-alanyl is preferred as the amino acid in the non-carrying units of the peptide chain. The dipeptides are most useful.

The compounds of this invention are exemplified by the following structural formula:

$$\underset{\underset{\text{②}}{P-NHCHCNHCHCOQ}}{\overset{R^1\ O\ W}{|\ \|\ |}} \qquad I$$
$$\phantom{P-NHCHCNHCHCOQ}\ \text{①}$$

in which:
- $R^1$ is $C_{1-4}$ lower alkyl, phenyl, ω-amino-$C_{2-4}$-alkyl or benzyl;
- P is a hydrogen, carbobenzoxy or from 1–4 residue units of an amino acid such as glycyl, phenylglycyl, alanyl, phenylalanyl, lysyl, ornithyl, norvalyl, valyl, norleucyl, isoleucyl or leucyl, either in the natural L- or in the D-configuration; and
- Q is hydroxy, benzyloxy or from 1–4 residue units of an amino acid such as glycyl, phenylglycyl, alanyl, phenylalanyl, lysyl, ornithyl, norvalyl, valyl, norleucyl, isoleucyl or leucyl, either in the natural L- or in the D-configuration; and
- W is a residue of a pharmaceutically useful agent (HW) having an electron configuration capable of participating in a nucleophilic displacement reaction, said residue being reversibly substituted and being derived from an antimicrobial or an antiparasitic agent.

In structural formula I, the 2-peptide unit will be recognized as an alanyl (or related valyl, norvalyl, leucyl, isoleucyl or norleucyl), phenylglycyl, lysyl, onithyl or phenylalanyl group, respectively.

Also, in the oligopeptide fragments, P and Q each peptide unit may be different in configuration or in chemical structure, however, for convenience in preparation, it is preferred that the units be the same and that they be simple in structure, for example, poly-L-alanyl or even polyglycyl units.

Any reactive groups, on either an amino acid member of the peptide chain or on the warhead group, may be protected during synthesis similarly to those referred to in the EPO reference, at page 7, line 15 and page 12, line 14. Also, see U.S. Pat. No. 3,803,120, especially at column 4, line 28 as well as columns 6–9, or U.S. Pat. No. 3,957,803.

Preferred compounds of this invention are those of the following formula:

$$\underset{NH_2CHCNHCHCO_2H}{\overset{CH_3\phantom{XXXXX}}{\underset{\phantom{X}}{|}\phantom{XX}\overset{O}{\underset{\|}{\phantom{X}}}\ \overset{W}{\underset{|}{\phantom{X}}}}} \qquad IA$$

in which W is as defined for I above and the configuration is L,L.

HW, more specifically, is a compound represented by the following structural formula:

$$H-X-R^2 \qquad II$$

in which:
X is —O—, —S—, —NH—, $$-N\!\!\diagup^{\phantom{X}}_{\diagdown}$$

or activated $$-CH\!\!\diagup^{\phantom{X}}_{\diagdown};$$

and
$R^2$ is the residue of a pharmaceutically useful agent which is a nucleophilic attacking group when taken with X.

The active agent is, more specifically, an antimicrobial or anti-parasitic agent, for example;

(A)

[Structures: HS-pyridyl, HS-pyridyl N-oxide, HS-C₆H₄-NO₂, HS-C₆H₃(NO₂)₂, HS-C₆H₃(NO₂)(CO₂H), HS-thiadiazole with N-CH₃, H₂N-pyrimidine-NH₂ with CH₂-aryl(OCH₃)₃ and NH₂]

-continued

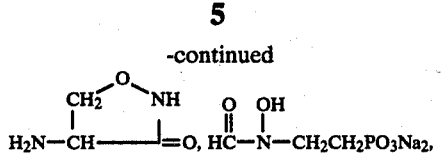
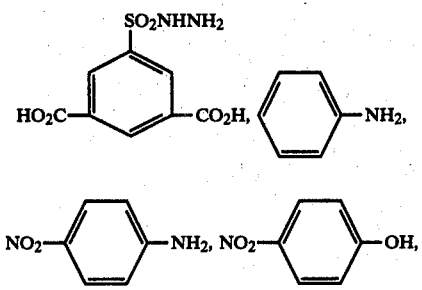
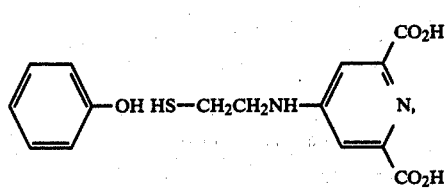
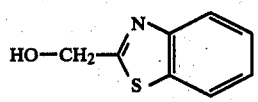
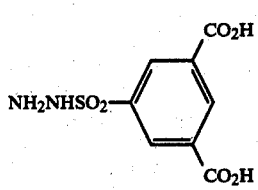

as well as;

(B) a $C_{1-6}$-alkylthio, a functionalized $C_{1-6}$-alkylthio such as ω-amino-$C_{2-6}$-alkylthio, or a phenylthiol such as

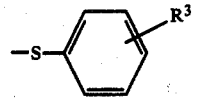

wherein $R^3$ is H or from 1-2 substituents of the group comprising $C_{1-4}$-alkyl, $C_{1-4}$-alkoxy, cyano, halo or $C_{1-4}$-alkylthio. See also CA 94 185507c, CA 93 150163q, CA 93 114552q; CA 86 89671r; CA 90 98007p; CA 90 152197r; CA 92 146609b, EPO No. 38,541, U.S. Pat. Nos. 3,590,035; 3,700,676 or 3,773,770 for other antimicrobial warheads, as well as;

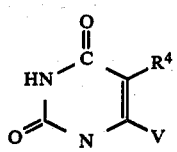

wherein $R^4$ is hydrogen, halo, carboxy, trifluoromethyl, Z-bromovinyl, or nitro and V is hydrogen or carboxy, as well as;

(D) oxibendazole, parbendazole, oxfendazole, cambendazole, oncodazole, fenbendazole, mebendazole, albendazole or thiabendazole.

Preferred compounds to be used as warhead residues or releasable moieties in the antimicrobial or antiparasitic fields are albendazole or orotic acid derivatives.

The compounds of formula I or IA in which W is a $C_{1-6}$-alkylthio, a functionalized $C_{1-6}$-alkylthio for example a $C_{1-6}$-aminoalkylthio or a phenylthio as defined above by formula II are of particular utility for detecting protease/peptidase activity in biological systems. For example, the compounds are more sensitive chromogenic detectors of protease activity in biological liquids, such as serum, than is leucine p-nitroanilide. This utility depends on the release, by protease action, of the mercaptan, H-S-$R^2$, which is assayed quantitatively by colorimetry using Ellman's reagent as described in the examples.

L-Alanyl-L-(α-phenylthio)glycine, for example, was used as a detector peptide to determine protease activity in fresh and aged mouse serum where the use of leucine p-nitroanilide as chromogenic substrate detects little difference in protease level.

Detector compounds of this invention which have a free carboxy in their structures are used to act as chromogenic substrates for carboxypeptidases in biological fluids. N-acetyl-L-alanyl-L-(α-phenylthio)glycine is used to monitor the action of carboxypeptidase A using Ellman's methodology.

Detector peptides of this invention such as L-alanyl-L-(α-phenylthio)glycine have been successfully used as enzyme substrates for leucine aminopeptidase and aminopeptidase M. These detector peptides, for example, CBZAlaGly(S(CH$_2$)$_3$NH$_2$)OBn, have also been shown to be substrates for trypsin.

The chemical compounds of this invention are prepared by the following reaction sequences:

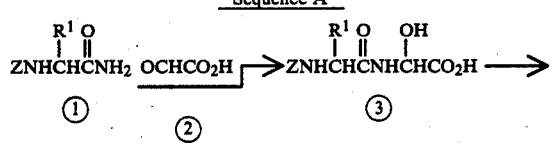
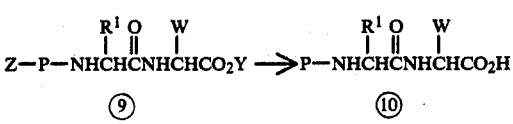

-continued

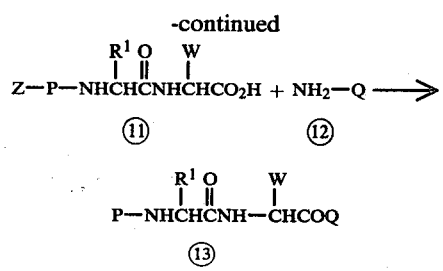

In the reaction sequence, W, P, Q, R¹, X and R² are as described above or protected derivatives of the same as is conventional in the peptide art.

Z is an amino protecting agent which is used in the polypeptide art to protect a sensitive chemical center during a reaction sequence and is, thereafter, removed by chemical means which will not affect the rest of the molecule, especially, in this case, the α-substituent, W. Such amino protective groups may be those removable either by selective hydrolysis or exchange hydrogenolysis over a noble metal, such as palladium, in the presence of a hydrogen donor. Examples of these groups are aralkyl- or alkyloxycarbonyl groups, for example, trichloroethyloxycarbonyl, allyloxycarbonyl, benzhydryloxycarbonyl, benzyloxycarbonyl or a tert.-butyloxycarbonyl (t.-boc) type. A protective group which can be removed by the same chemical reaction as the carboxyl protective group, referred to below, is preferred. See the references mentioned above for other protective devices known to the peptide art.

Y is a carboxylic acid protecting group which is used for the same purpose as Z is used for amino. Examples of such groups are the easily split esters such as allyl, benzhydryl, tert.-butyl, trichloroethyl, benzyl, benzyloxymethyl or p-nitrobenzyl esters.

Ac is an acyl group which, together with the oxygen to which it is attached, forms an active acyloxy leaving group known to the art. Examples of alkyl or arylcarbonyloxy groups are alkanoyl of 2-6 carbons, benzoyl, $C_{1-6}$-lower alkylsulfonyl, for example, mesyl, or $C_{6-10}$-arylsulfonyl, for example, p-toluenesulfonyl. Certain leaving groups, such as the tosyloxy, may be so reactive that intermediate compounds containing them are not easily isolated. These may be formed and used without isolation. Alternatively, a halo leaving group is used in place of the acyloxy groups, such as an α-chloro or α-bromo group.

Examples of protective groups which are useful for synthesis of peptides and which can be used here for Z and Y, as well as for protecting other chemically sensitive groups in P or W, are given in Synthetic Peptides I, Von Nostrand, 1970, pages 3-8 and in succeeding volumes in this series as well as in those references mentioned above.

For convenience, Z and Y are, essentially, the same protective groups which are both removable by a hydrogen exchange reaction over a palladium catalyst in the presence of a standard hydrogen donor. Examples of protected intermediates are those of reaction Sequence A which have (1) Z as carbobenzoxy and Y as benzyl, (2) Z as allyloxycarbonyl and Y as allyl, or (3) Z is tert.-butyloxycarbonyl and Y is tert.-butyl. Also, when —OAc is displaced, the most practical group for Ac is acetyl. A further modification is to replace the α-OH group in compound 3 of Sequence A with a halo leaving group, such as chloro or bromo, using halogenating agents known to the art. The halo ion is, then, the leaving group in the displacement reaction, 4→6. The α-halo intermediates are particularly of interest when the warhead group is to be attached to the peptide chain via an oxy atom. Metallic salts of the attacking oxy group are, then, useful.

In reaction Sequence A, the initial reaction comprises reacting a L-α-substituted amino acid amide (1) with glyoxylic acid (2) itself or with a glyoxylate ester in which the carboxyl protective group, as described above, is already in place. The reaction is carried out, at from room temperature to reflux, until the reaction is complete, such as for up to 8 hours, in an inert organic solvent in which the reactants are substantially soluble. Benzene-like solvents, refluxed over a water trap, are most convenient. Also, halogenated solvents, such as methylene chloride, or ethereal solvents, such as ethyl ether, may also be used.

The resulting α-hydroxydipeptide (3), if not already esterified, is then reacted with a carboxy blocking agent as known to the art.

The blocked α-hydroxydipeptide is reacted with an acylating agent such as an acyl chloride or anhydride in the cold in a tertiary amine, such as pyridine, to give the α-acyloxydipeptide (4).

The α-acyloxydipeptide (4) is reacted with a nucleophilic, biologically-active agent, $HXR^2$ or HW, in an inert organic solvent in which the reactants are soluble, at from room temperature up to reflux temperature, until reaction is complete. A tertiary amine may be present to take up the displaced acid. Dimethylformamide, dioxane, tetrahydrofuran or dimethylacetamide, each combined with an excess of triethylamine, are good solvent systems.

We have found that the α-acyloxy group of the compounds of formula 4 of reaction sequence A is very susceptible to nucleophilic displacement. The reaction favors a $SN_2$ course of reaction rather than a mixed $SN_2$-$SN_1$ course reported in the Tanabi references. Generally speaking, the α-acyloxy group of the compounds of formula 4 will undergo replacement much like that in the 3-acetoxymethyl group of certain cephalosporin intermediates, see Cephalosporins and Penicillins, E. H. Flynn, Academic Press, (1972) pages 158-164 and 151-171.

The displacement of the α-acyloxy group of the dipeptide is a key reaction of this invention. As stated in the discussion of the prior art above (T. Nishitani, et al.), such displacements have been previously reported using an N-acyl amino acid having N-acyl groups common to the art, such as acetyl, isobutyryl or carbobenzoxy. These would not, however, serve as support moieties as do the peptide chains of the novel compounds, described herein, which must possess the critical carrying peptide unit in the L-configuration as well as the N-terminal amino group and the stabilizing 2-unit. In practice, the course of the displacement is followed by thin layer chromatography to ascertain the progress of the reaction.

The important dipeptide products of the displacement (6) are then reacted to remove any protective groups if the operator so desires, as known to the art, such as by a catalytic exchange reaction (for example, using a palladium catalyst with a hydrogen source), acid treatment (for example, using hydrogen chloride or hydrogen bromide in acetic acid), catalytic hydrogenation if suitable, or alkaline treatment (for example, using calcium hydroxide). Of course, such treatment must not induce chemical splitting at the critical α-warhead moiety (W). When the protecting groups have been removed, the end compounds of this invention of the dipeptide family (formula I, P=H) are obtained.

The oligopeptides which have more than the two amino acid units at 1 and 2 are most conveniently prepared by condensing an amino acid or oligopeptide which has been N-protected as known to the art with the N-deblocked α-warhead dipeptide (Sequence A, compound 8). This step, once again, uses any peptide coupling method known to the art (see, for example, U.S. Pat. No. 3,803,120). Examples of such methods are using the N-blocked amino acid and the C-blocked dipeptide with dicyclohexylcarbodiimide or carbonyldiimidazole. Other coupling methods use various active coupling forms of the oligo acid such as acyl halides, anhydrides, azides or active mixed esters. Once again, after the peptide coupling reaction, the protective groups are removed as described above to obtain the final prodrugs of structural formula I.

If the peptide chain is to be extended toward the C-terminus, the desired protected amino acid or oligopeptide unit is reacted with the protected α-substituted oligopeptide, 11, as described immediately above and for Sequence B above.

As an alternative, the oligopeptide chain desired for the final product may be in place in the structure corresponding to compound 1 of Sequence A at the glyoxalate condensation step and, then, carried through to the end product. This method, however, is not preferred since the intermediate compounds often have physico-chemical properties which make them difficult to handle.

The products of the chemical reactions, outlined in reaction Sequences A and B, are obtained as diastereoisomeric mixtures. These are separated, if desired by one utilizing this invention, by prior art methods such as reverse phase chromatography or fractional crystallization of either the oligopeptides (I) themselves or their salts with optically pure bases or acids. The chromatographic separation of isomers has been found, unexpectedly, a convenient resolution method. The L,L-isomers at the 1 and 2 amino acid units are the ones which are selectively transported by the peptide permease system of the cell membrane. If a mixture of isomers is present, the L,L-isomers are absorbed selectively, leaving the impermeable L,D-isomers behind. Therefore, either separated L,L-isomers or diastereoisomeric mixtures are useful, with appropriate adjustments in the active quantities of the warhead moiety based on this observation.

The reactions, outlined above, are intended to be carried out in liquid phase, however, as with most peptide reactions, solid phase or enzyme technology may be used alternatively, R. B. Merrifield, Biology 3 1385 (1964) or J. Am. Chem. Soc. 85 2149 (1963).

Also included in this invention are the following chemical intermediates which have structures whose key feature is a potentially displaceable substituent at the α- or 2-position of the terminal glycyl unit which is, in turn, combined with the stabilizing amino acid unit as the other unit of the dipeptide;

in which Y, Z and $R^1$ are as described above; and $R^5$ is a leaving group as known to the chemical art in nucleophilic displacement reactions, for example, chloro, bromo, hydroxy or acyloxy, with acyl being as described above.

Advantageous intermediates are those of formula III in which $R^1$ is methyl, $R^5$ is hydroxy or acetoxy; Z is allyloxycarbonyl, carbobenzoxy or tert.-butyloxycarbonyl, and Y is allyl, benzyl or tert.-butyl.

The prodrugs of formula I are used to enhance permeability of the cell membrane of the target organism, against which the carried chemotherapeutic residue (the warhead, W) is active. The compound of formula I is brought into contact with the target cells, either in vitro, such as in treating a surface bacterial or fungal infection by direct contact, or in vivo, such as in treating a systemic or localized infection by local infusion, parenteral injection or oral administration.

The dose of the prodrug is derived from the known dose of the warhead or drug itself compensated for the inactive peptide carrying chain of the prodrug. Of course, if a topical application of an antibacterial-antifungal prodrug is used, the dose is less important than is a sufficient excess quantity of drug applied to the site of infection. For topical use, from 0.5–10% concentration of prodrug is used in solution, in suspension or in a locally applied product from such as in an ointment, shampoo, hair oil, troche, gum, drench or soap.

The applied prodrug, then, is transported through the cell membrane by means of the affinity of the peptide backbone to the receptor units of the permease system of the membrane. When inside the cell, the prodrug is attacked by intracellular peptidases to split the oligopeptide chain, at least between the 1 and 2-units:

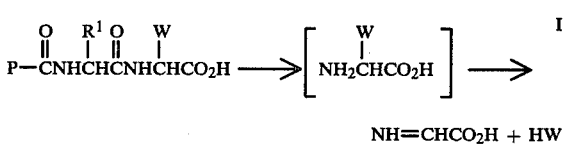

in which P and W are as defined above. The drug is, then, released at the site of action within the cells by disassociation of the α-substituted amino acid. Since the cell membrane is not easily permeable to the active agent, the latter will tend to build up within the cell. Also, if the warhead (W) is a very large moiety or carries a charged group, it may not be easily transported. In this case, the number of peptide units in the carrying chain should be increased. Thus, the prodrug is able to use the non-specific oligopeptide transport system. In the case of an interferring group such as an acid group, it might be masked reversibly or compensated for by using amino acid units which are positively charged at physiological pH's, such as lysine.

While these new compounds are most useful in treating bacterial or fungal microbes topically, or even systemically in a whole animal, the same prodrug concept can be used for other purposes. For example, the peptide prodrug can be used to prepare injectable preparations of compounds not normally so used because of physico-chemical properties such as low solubility. This utility may be particularly applied to known benzimidazole anthelmintics. Of course, any route of administration which exposes the prodrug to peptidases prior to reaching the site of action will destroy the peptide chain of the prodrug. This effect may be, in fact, beneficial, as with certain anthelmintics (i.e. oxybendazole, albendazole, oncodazole).

The prodrugs of formula I are represented herein as their amphoteric polypeptide forms. One skilled in the art will recognize that salt forms of the prodrugs may be equally useful, such as pharmaceutically acceptable acid addition salts when a basic center is present in the polypeptide chain or in the carried warhead. Alternatively, pharmaceutically acceptable basic salts derived from the usual bases, such as those having alkali metal or nontoxic organic amine cations, can be prepared if an acid center is present. Both types of salts are prepared as known to the art, usually by contacting the prodrug with an excess of acid or base in a suitable solvent.

Furthermore, as stated hereinabove, the compounds of formulas I and IA can be used in the form of an amide derivative at the N-terminus such as an N-acetyl, carbobenzoxy or allyloxycarbonyl derivative or an ester derivative at the C-terminus such as an alkyl, benzyl or alkyloxy derivative.

The following examples are designed to teach the preparation of the compounds of this invention as well as the biological activity of representative compounds of this invention. All temperatures are in degrees Centigrade.

EXAMPLE 1

A mixture of 5 g (0.0225 m) of N-carbobenzoxyalanylamide, 2.3 g (0.025 m) of glyoxylic acid hydrate and 50 ml of ethyl ether-methylene chloride was allowed to stand with stirring overnight. A white solid, N-carbobenzoxy-L-alanyl-D,L-2-hydroxyglycine, separated which weighed 2.0 g, m.p. 128°–130°. The filtrate was further reacted with 2.3 g of glyoxylic acid to obtain 3.15 g of additional product, m.p. 127°–130°.

Anal. Calcd. for $C_{13}H_{16}N_2O_6$: C, 52.70; H, 5.44; N, 9.46. Found: C, 52.65; H, 5.06; N, 9.57.

A solution of 0.59 g (2 mm) of the α-hydroxydipeptide in 20 ml of dimethylformamide was mixed with a solution of 0.33 g (1 mm) of cesium carbonate in 8 ml of water. The pH of the mixture was brought up to ~7.0. The volatiles were taken off with evaporation and, then, successively azeotroping with dimethylformamide and toluene. The resulting gummy solid was dissolved in 20 ml of dimethylformamide and 1.71 g (10 mm) of benzyl bromide is added. The mixture was stirred at room temperature overnight.

The filtrate was diluted with water, then extracted with ethyl acetate. The washed extracts were combined and evaporated. The residue was triturated under ether to give 0.49 g of white solid N-carbobenzoxy-L-alanyl-D,L-2-hydroxyglycine, benzyl ester. A sample was purified over silica gel using 5% methanol/methylene chloride, m.p. 91°–91.5°.

Anal. Calcd. for $C_{20}H_{22}N_2O_6$: C, 62.17; H, 5.74; N, 7.25. Found: C, 62.20; H, 5.36; N, 7.04.

This reaction was also carried out using benzyl bromide, sodium bicarbonate and dimethylformamide to give a good yield of the desired benzyl ester.

Acetic anhydride (3.3 ml) was added to a mixture of 0.27 g (7 mm) of the blocked α-hydroxydipeptide and 3.3 ml of pyridine cooled to 0°. After standing in the cold overnight, the reaction mixture was evaporated. The residue was triturated with ether to give 0.32 g of white N-carbobenzoxy-L-alanyl-D,L-2-acetoxyglycine, benzyl ether.

Anal. Calcd. for $C_{22}H_{24}N_2O_7$: C, 61.67; H, 5.65; N, 6.54. Found: C, 61.91; H, 5.65; N, 6.33.

The α-acetoxydipeptide (0.28 g, 6.8 mm) was reacted with 0.11 g (6.8 mm) of (benzothiazol-2-yl)methanol in 4 ml of tetrahydrofuran and 0.068 g of triethylamine at 20°, then, stirred 24 hours. The solvent was evaporated in vacuo to give a yellow oil, N-carbobenzoxy-L-alanyl-2-(benzothiazolyl-2-methoxy)-D,L-glycine, benzyl ester.

This material (150 mg) is treated with 5% palladium-on-charcoal as a catalyst and cyclohexene as a hydrogen donor in methanol to give L-alanyl-2-(benzothiazolyl-2-methoxy)-D,L-glycine.

EXAMPLE 2

A mixture of 0.53 g (1.23 mm) of the α-acetoxydipeptide of Example 1, 0.146 g (1.12 mm) of 5-fluorouracil, 0.113 g (1.12 mm) of triethylamine and 2 ml of dimethylformamide was stirred at room temperature for 18 hours. The mixture was concentrated. The residue was dissolved in 2 ml of water, then re-extracted with ethyl acetate. The combined extracts were washed, dried and concentrated to give 0.59 g (98%) of slightly impure N-carbobenzoxy-L-alanyl-2-(5-fluorouracil-1-yl)-D,L-glycine, benzyl ether.

This material was purified by medium pressure liquid chromatography using methylene chloride/1% methanol in methylene chloride and a silica gel column to give 0.45 g (74%) of pure product as a diastereoisomeric mixture, m.p. 93°–95°.

A mixture of 350 mg (0.70 mm) of the D,L-isomer mixture, 300 mg of 10% palladium-on-charcoal, 0.5 ml of cyclohexene and 35 ml of methanol was heated at reflux for 10 minutes. The hot mixture was filtered and concentrated to give a pure deblocked product of L-alanyl-2-(5-fluorouracil-1-yl)-D,L-glycine, 0.18 g (94%). High pressure liquid chromatography, using a reverse phase modified silica gel $C_{18}$ column with an eluent of 20% methanol-water, demonstrated two diastereoisomers in 1-1 ratio.

Anal. Calcd. for $C_9H_{11}FN_4O_5.H_2O$: C, 36.95; H, 4.48, N, 19.17. Found: C, 36.66, H, 4.34, N, 18.85.

The L-L and L-D diastereoisomers were separated by medium pressure liquid chromatography, after deblocking, over the silica gel column using the solvent system described above.

The L-D isomer had a rotation as follows: $[\alpha]_D^{25}$ (1, $H_2O$) = −105.9°.

Anal. Calcd. for $C_9H_{11}FN_4O_5.H_2O$: C, 36.99, H, 4.48, N, 19.17. Found: C, 37.11; H, 4.14; N, 19.19.

The L-L isomer, had a rotation as follows: $[\alpha]_D^{25}$ (1, $H_2O$) = +131.1°.

Anal. Calcd. for $C_9H_{11}FN_4O_5.1.5H_2O$: C, 35.89, H, 4.68; N, 18.59. Found: C, 35.54, 35.54; H, 4.20, 4.08; N, 18.44, 18.51.

EXAMPLE 3

Allyl glyoxylate acetal, b.p. 55°–60° at 16 mm/Hg, was prepared by reacting glyoxylic acid hydrate with an excess of allyl alcohol in benzene.

Allyloxycarbonylamino-L-alanylamide, m.p. 135°–136°, was prepared by reacting L-alanylamide hydrochloride with one equivalent of allyl chloroformate in 20 ml of water containing 2.0 g of sodium hydroxide and 4 ml of tetrahydrofuran.

Anal. Calcd. for $C_7H_{12}N_2O_3$: C, 48.83; H, 7.03; N, 16.27. Found: C, 49.16; H, 7.12; N, 16.10.

A mixture of 1.54 g (0.009 m) of the allyloxycarbonylamino-L-alanylamide, 1.2 g (0.009 m) of allylglyoxylate acetal and 50 ml of benzene was heated at reflux using azeotropic conditions for 54 hours to complete the reaction. The cooled mixture was treated with petroleum ether and triturated to separate 2 g (80%) of crystalline N-allyloxycarbonyl-L-alanyl-2-hydroxy-D,L-glycine, allyl ester. Purification by recrystallization from ethyl acetate/petroleum ether gave 1.1 g of white solid, m.p. 88°–90°.

Anal. Calcd. for $C_{12}H_{18}N_2O_6$: C, 50.35; H, 6.34; N, 9.88. Found: C, 50.25; H, 6.55; N, 10.43.

A mixture of 0.9 g (0.003 m) of the α-hydroxydipeptide, 7.0 ml of acetic anhydride and 9 ml of dry pyridine was prepared in the cold. After standing 8 hours, the volatiles were taken off in vacuo to leave 0.85 g of yellow oil. Thin layer analysis showed some starting material present which was separated by trituration with ether to give N-allyloxycarbonyl-L-alanyl-2-acetoxy-D,L-glycine, allyl ester. NMR (CDCl$_3$), δ, 1.35 (d,3); 2.0 (s,3); 4.5 (t,2) 5–6 (m$^3$, olefinics); 6.4 (d,2).

A mixture of 0.75 g (0.0022 m) of the α-acetoxydipeptide, 0.25 g (0.0022 m) of benzothiazol-2-ylmethanol and 10 ml of dry tetrahydrofuran was added to 0.22 g (0.0022 m) of dry triethylamine in 5 ml of dry tetrahydrofuran. The mixture was stirred at room temperature for 8 hours. Thin layer chromatography (99:1, methylene chloride:methanol) showed the reaction was complete. The mixture was evaporated in vacuo to give 1.1 g of yellow oil, which was purified by medium pressure liquid chromatography over a silica gel column (2% methanol in methylene chloride), to give 0.51 g (54%) of N-allyloxycarbonyl-L-alanyl-2-(benzothiazolyl-2-methoxy)-D,L-glycine, allyl ester. NMR (CDCl$_3$), δ, 1.4 (d,3); 4.55 (t,2); 5.15 (s,2); 5.2–6.2 (m$^3$, olefinics); 7.4 and 8.0 (m, aromatics).

A mixture of 0.3 g (0.0007 m) of the displacement product and 3 ml of dry methylene chloride under nitrogen was treated with a solution of 0.5 g of 2-ethylhexanoic acid, as hydrogen donor, in 3 ml of methylene chloride, followed by 40 mg of triphenylphosphine and 40 mg of tetra(triphenylphosphine)palladium. The mixture was stirred at room temperature overnight, then, diluted with ether. The resulting solid (18 mg) was collected.

The filtrate was concentrated to leave a residue which was largely starting material.

This material was reacted again, as above, for 24 hours, to give 85 mg of deblocked product, to give a total yield of 103 mg of L-alanyl-2-(benzothiazolyl-2-methoxy)-D,L-glycine as the zwitterion, Rf 0.47 (80:20 acetonitrile/water).

Anal. Calcd. for $C_{13}H_{15}N_3O_4S$: C, 50.48; H, 4.89; N, 13.58. Found: C, 50.70; H, 4.84; N, 13.40.

EXAMPLE 4

A mixture of 0.28 g (0.001 m) of 4-(N-(2-mercaptoethyl)amino)-pyridine-2,6-dicarboxylic acid, 0.33 g (0.001 m) of the blocked α-acetoxydipeptide from Example 3, 0.44 g (0.004 m) of dry triethylamine and 13 ml of dry dimethylformamide was stirred at room temperature for two hours. Some unreacted amine salt of the cysteamine starting material was separated. The filtrate was evaporated to leave a residue which was dissolved in water, acidified to pH 1.5 and allowed to evaporate overnight. A solid, 105 mg, separated which was the desired free base, N-allyloxycarbonyl-L-alanyl-2-(2,6-dicarboxy-pyridyl-4-)ethylthio-D,L-glycine, allyl ester. NMR (DMSO-d$_6$), δ, 1.2 (d,3); 2.85 (m,2); 3.5 (m,2); 4.2 (t,1); 4.5 (m,2); 5.1–6.1 (m$^3$, olefinic); 7.4 (s,2).

Anal. Calcd. for $C_{21}H_{26}N_4O_9S$: C, 48.63; H, 4.97; N, 10.65. Found: C, 49.30; H, 5.13; N, 10.97.

A mixture of 220 mg (0.0004 m) of the blocked cysteamine displacement product, 0.09 ml of triethylamine and 10 ml of dry methylene chloride was reacted with 0.66 g of 2-ethylhexanoic acid in 3 ml of dry ethyl acetate, followed by 20 mg each of triphenylphosphine and tetra(triphenylphosphine)palladium. The mixture was stirred overnight. The separated white solid was collected, washed with methylene chloride and dried to give 150 mg (97%) of L-alanyl-2-(2,6-dicarboxy-pyridyl-4-)-ethylthio-D,L-glycine as the monotriethylamine salt; U.V. Emax=11,000 at 300 wave lengths in water.

Anal. Calcd. for $C_{14}H_{18}N_4O_7S.N(C_2H_5)_3$: C, 49.27; H, 6.82; N, 14.37. Found: C, 49.13; H, 6.80; N, 14.71.

EXAMPLE 5

A mixture of 0.175 g (0.64 mm) of L-alanyl-2-(5-fluorouracil-1-yl)-D,L-glycine hydrate, prepared as above, 0.1089 of sodium bicarbonate and 2.5 ml of water was combined with 0.204 g (1.28 mm) of N-carbobenzoxy-L-alanine, N-hydroxysuccinimide ester, prepared from the blocked alanine and N-hydroxysuccinimide carbonate, dissolved in 3 ml of dioxane. The mixture was stirred at room temperature for 5 hours, then concentrated. The residue was diluted with 7 ml of water and 7 ml of ethyl acetate, then, adjusted to pH 3.2 with 10% citric acid solution. The organic layer was separated and combined with ethyl acetate washings of the aqueous layer, then, washed with 10% citric acid solution. The dried organic extract was evaporated to give 0.15 g (50%) of a white solid, which is N-carbobenzoxy-L-alanyl-L-alanyl-2-(5-fluorouracil-1-yl)-D,L-glycine.

This material (0.15 g) was dissolved in 15 ml of methanol and heated at reflux with 0.15 g of palladium-on-charcoal and 0.5 m of cyclohexene for 10 minutes. The hot reaction mixture was filtered, concentrated, redissolved in water and lyophilized. The product was, then, purified on a C-18 silica gel reverse phase medium pressure liquid chromatographic column (H$_2$O) to give, after lyophilizing, L-alanyl-L-alanyl-2-(5-fluorouracil-1-yl)-D,L-glycine.

Anal. Calcd. for $C_{12}H_{16}N_5O_6.2H_2O$: C, 37.80; H, 5.28; N, 18.36. Found: C, 37.98; H, 4.78; N, 18.05.

EXAMPLE 6

A mixture of 0.328 g (1.0 mm) of N-allyloxycarbonyl-L-alanyl-2-acetoxy-D,L-glycine, allyl ester and 0.249 g (1.0 mm) of oxibendazole (methyl 5-n-propoxy-2-benzimidazolecarbamate), 0.10 g of triethylamine and 5 ml of dimethylformamide is stirred at room temperature for 12 hours. To the resulting mixture was added 50 ml of ethyl acetate followed with 50 ml of 1.5% hydrochloric acid. The ethyl acetate fraction was separated and washed with water and brine in succession. The dried extract was concentrated to give 0.305 g (59%) of N-allyloxycarbonyl-L-alanyl-2-(5-n-propoxy-2-carbomethoxyaminobenzimidazol-1-yl)-D,L-glycine, allyl ester. Thin layer chromatography over silica gel (95:5 methylene chloride/methanol) shows one major product. This material was further purified using the medium pressure liquid chromatography over silica gel, using methylene chloride to 2% methanol in methylene chloride to give 0.166 g of purified product.

This blocked product (0.157 g, 0.30 mm) was combined with 50 mg of tetra(triphenylphosphine) palladium, 10 mg of triphenylphosphine and 5 ml of ethyl acetate as above. The mixture was stirred under nitrogen for 3 hours. The separated product (50 mg) was purified by recrystallization from aqueous acetone to give L-alanyl-2-(5-n-propoxy-2-carbomethoxyaminobenzimidazol-1-yl-D,L-glycine. The compound demonstrated two ultra-violet and ninhydrin positive spots on thin layer, indicative of the two diastereoisomers.

This compound, 10 mg/kg of warhead equivalent, is dissolved in silane and administered by subcutaneous injection to a swine or horse infected with a helminth infestation susceptible to oxibendazole.

Other benzimidazoles having a reactive hydrogen at the 1-position, as listed above, may be prepared and used similarly. The dipeptide chain (I, n=o) is preferred for injectable use because of the good solubility of the resulting prodrug.

EXAMPLE 7

A mixture of 0.214 g (0.05 mm) of the blocked 2-acetoxyglycine of Example 1 and 2 ml of dry tetrahydrofuran was mixed with a solution 0.11 g (0.1 mm) of 2-mercaptopyridine, 0.119 (0.1 mm) of triethylamine and 5 ml of tetrahydrofuran. The latter solution was added dropwise, over a 20 minute period, to the acetoxy mixture. The reaction mixture was stirred at ambient temperature overnight.

The solvents were combined and evaporated to give a yellow oil which was taken up in ethyl acetate, washed with water and brine, then dried. The extract was evaporated to leave a yellow oil. NMR spectrum analysis showed the desired displacement product with a trace of starting acetate. Liquid chromatography using 5% methanol:methylene chloride demonstrated the separation of isomers.

N-Carbobenzoxy-L-alanyl-2-(pyridyl-2-thio)-D,L-glycine, benzyl ester (200 mg) was dissolved in glacial acetic acid and dry hydrogen chloride gas was bubbled through the mixture for 4 hours. Thin layer demonstrated only partial splitting. Hydrogen bromide gas was bubbled through the mixture. An exothermic reaction occurred in the mixture which was cooled in an ice bath. The blocked product disappeared quickly as analyzed by thin layer chromatography (cellulose plate, 4:1:4, butanol/acetic acid/water).

The mixture was concentrated and triturated with ether to give 0.132 g of L-alanyl-2-(pyridyl-2-thio)-D,L-glycine. This material contained minor quantities of impurities so it was passed through C-18 reverse phase medium pressure liquid chromatographic purification.

This same procedure is used using 2-mercaptopyridone as the displacing warhead to give D,L-alanyl-2-(1-oxypyridyl-2-thio)-D,L-glycine.

EXAMPLE 8

A mixture of 12.2 g (0.055 m) of carbobenzoxyalanylamide, 10 g (0.061 m) of benzyl glyoxalate and 150 ml of toluene was heated under vacuum at about 70° overnight, allowing the mixture to reflux over a water trap. The toluene was evaporated from the reaction mixture to give a white solid. This was treated with ethyl acetate. The dried extract was cooled to give 12.6 g of N-carbobenzoxy-L-alanyl-D,L-2-hydroxyglycine, benzyl ester identical to the intermediate characterized in Example 1.

This compound (500 mg) is reacted with 1-methyltetrazol-5-thiol or 1-(2-methanesulfonamidoethyl)tetrazol-5-thiol followed by acid treatment as described above to give D,L-alanyl-2-(1-methyltetrazolyl-5-thio)-D,L-glycine and D,L-alanyl-2-(1-(2-methanesulfonamido)ethyltetrazolyl-5-thio)-D,L-glycine.

EXAMPLE 9

A mixture of 0.386 g of N-carbobenzoxy-L-alanyl-2-hydroxy-D,L-glycine, benzyl ester, from Example 1 and 10 ml of thionyl chloride was stirred at room temperature overnight, then concentrated. The residue was triturated with petroleum ether to give, after filtration and drying, 0.364 g of N-carbobenzoxy-L-alanyl-2-chloro-D,L-glycine, benzyl ester.

Anal. Calcd. for $C_{20}H_{21}ClN_2O_5$: C, 59.33; H, 5.23; N, 6.92; Cl, 8.76. Found: C, 59.20; H, 5.38; N, 7.08; Cl, 8.68. The NMR spectrum showed a proton peak at 6.28 ppm. The α-hydroxy peak is at 5.55 ppm.

The halogenation was repeated using dimethoxyethane as solvent and a reflux period overnight. After thin layer analysis, the reaction mixture was combined with 35.2 mg of the disilver salt of (−)-(cis-1,2-epoxypropyl)phosphonic acid (prepared from the sodium salt in water, U.S. Pat. No. 3,929,840). The mixture was stirred overnight, then filtered and concentrated to give an oil. The product was dissolved in ethyl acetate, washed with water, dried and concentrated to leave 29.4 g of N-carbobenzoxy-L-alanyl-2-(−)-(cis-1,2-epoxypropyl)phosphono-D,L-glycine, benzyl ether which is a compound with phosphonomycin as the warhead.

This compound is deblocked using exchange hydrogenation as described above.

EXAMPLE 10

A mixture of 1.2 g (0.0036 m) of N-allyloxycarbonyl-L-alanyl-2-acetoxy-D,L-glycine, allyl ester, prepared as in Example 3, and 15 ml of dry dimethylformamide was mixed with 0.5 g (0.0036 m) of p-nitroaniline and 0.36 g (0.0036 m) of dry triethylamine. The mixture was stirred at room temperature for 67 hours, then poured into 300 ml of ice-water and stirred. The precipitated yellow solid was collected, washed with water and dried to give 1.22 g (83.5%) of N-allyloxycarbonyl-L-alanyl-2-(p-nitroanilino)-D,L-glycine, allyl ester. The product is recrystallized from hot methylene chloride, m.p. 160°–161°.

Anal. Calcd. for $C_{18}H_{22}N_4O_7$: C, 53.70; H, 5.46; N, 13.79. Found: C, 52.92; H, 5.56; N, 13.72.

A mixture of 0.366 g (0.0009 m) of the displacement product and 10 ml of methylene chloride was mixed with a mixture of 0.33 g of 2-ethylhexanoic acid and 10 ml of ethyl acetate followed by 0.04 g of triphenylphosphine and 0.04 g of palladium tetra(triphenylphosphine). After stirring for 20 hours, the mixture was worked up as described above to give 30 mg of L-alanyl-2-(p-nitroanilino)-D,L-glycine, m.p. 174°–175° (dec.).

Anal. Calcd. for $C_{11}H_{14}N_4O_5$: C, 46.81; H, 5.00; N, 19.85. Found: C, 48.73; H, 5.41; N, 18.65.

EXAMPLE 11

The α-acetoxypeptide used in Example 10, 0.66 g, was reacted with 0.28 g of p-nitrophenol as described to give 0.16 g of white solid, N-allyloxycarbonyl-L-alanyl-2-(p-nitrophenoxy)-D,L-glycine, allyl ester, m.p. 121°–122°.

Deblocking using the hydrogenation exchange procedure of Example 10 gave L-alanyl-2-(p-nitrophenoxy)-D,L-glycine, m.p. 105°–108°, slightly contaminated with unblocked starting material.

EXAMPLE 12

A mixture of 0.26 g (0.001 m) of 5-hydrazinosulfonyl-1,3-benzenedicarboxylic acid, 0.43 g (0.001 m) of N-carbobenzoxy-L-alanyl-2-acetoxy-D,L-glycine, benzyl ester and 5 ml of dry dimethylformamide is mixed with 0.3 g (0.003 m) of triethylamine. The mixture was stirred at room temperature for 4 hours. Thin layer (cellulose, 97:3:3-methylene chloride:methanol:formic acid) demonstrated starting materials were gone with a new spot present.

The volatiles were removed at the pump. The residue was treated with dilute hydrochloric acid. The separated oil was taken up in ethyl acetate. The combined extracts were dried and evaporated in vacuo to give a glassy residue of N-carbobenzoxy-L-alanyl-2-(3,5-dicarboxyphenylsulfohydrazino)-D,L-glycine, benzyl ester which could not be crystallized but had a consistant NMR curve.

This material (0.54 g, 0.0008 m) in 300 ml of methanol was reacted with 1.0 ml of cyclohexene, 0.54 g of 10% palladium-on-charcoal at reflux for 1 hour. Working up as described above gave product which was not active in the biological screen described in the utility example but the product on further analysis was found to be not completely deblocked.

The material was deblocked as noted in Example 2, using a longer reaction time, to give the desired L-alanyl-2-(3,5-dicarboxy-phenylsulfohydrazino)-D,L-glycine,

EXAMPLE 13

A mixture of 2.14 g (5 mm) of N-carbobenzoxy-L-alanyl-D,L-2-acetoxyglycine benzyl ester, 0.55 g (5 mm) of thiophenol, 0.5 g (5 mm) of triethylamine and 25 ml of dimethylformamide was stirred at room temperature for 18 hours. The mixture was concentrated. The residue was dissolved in ethyl acetate. The organic extract was washed with water (3×50 ml), dried (MgSO$_4$), concentrated and flash chromatographed over silica gel to give 1.6 g (67%) of analytically pure oily N-carbobenzoxy-L-alanyl-2-(thiophenyl)-D,L-glycine benzyl ester as a mixture of diasteriomers.

A mixture of 1.4 g (2.9 mm) of blocked peptide prepared above was dissolved in 10 ml of glacial acetic acid and cooled to 0°. A 25 ml saturated solution of glacial acetic acid and hydrobromic acid was added to the cooled acetic acid solution of blocked peptide. The mixture was stirred for 30 minutes. The cooling bath was, then, removed and the solution stirred for 5 hours. Solvents were evaporated to produce a viscous solid (gum) which solidified on trituration with methylene chloride to give 0.4 g (54%) of a hygroscopic HBr salt. This solid salt was converted to the zwitterion by dissolving in ethanol and treating the resulting solution with 5 ml of propylene oxide which, after 5 hours, produced 0.2 g of a white solid, L-alanyl-2-(thiophenyl)-D,L-glycine.

High pressure liquid chromatography (HPLC) using a reverse phase modified silica gel C$_{18}$ column with a stepped eluent of 100% water (300 ml), 10% methanol-water (1 l), 20% methanol-water (1.5 l), separated the L-L and the L-D diastereoisomers.

The L-L isomer had a rotation as follows: $[\alpha]_D^{25}$ (1, H$_2$O) = +170.0.

Anal. Calcd. for C$_{11}$H$_{14}$N$_2$O$_3$S.¼H$_2$O: C, 51.05; H, 5.64; N, 10.82. Found: C, 51.37; H, 6.65; N, 10.42.

The L-D isomer had a rotation as follows: $[\alpha]_D^{25}$ (1, H$_2$O) = −200.8.

Anal. Calcd. for C$_{11}$H$_{14}$N$_2$O$_3$S.¼H$_2$O: C, 51.05, H, 5.64, N, 10.82. Found: C, 51.11; 5.65; N, 10.25.

EXAMPLE 14

The α-acetoxypeptide, which was used in Example 13, (5 mm) is reacted with 2,4-dichlorothiophenol (5 mm) using triethylamine (5 mm) in 25 ml of dimethylformamide to give the desired blocked peptide.

The carbobenzoxy and benzyl blocking groups are removed as previously described using hydrobromide acid, acetic acid to give the hydrobromide salt of the desired peptide which was converted to the zwitterion by treatment with propylene oxide. The isomers of L-alanyl-2-(2,4-dichlorothiophenyl)-D,L-glycine are separated as described in Example 13.

EXAMPLE 15

The α-acetoxypeptide from Example 13, (5 mm), 4-acetamidothiophenol (5 mm), triethylamine (5 mm) and 25 ml of dimethylformamide are reacted and resulting blocked peptide deblocked as described. The resulting diasteriomeric mixture is separated using high pressure liquid chromatography as described to give L-alanyl-2-(4-acetamidothiophenyl)-D,L-glycine.

EXAMPLE 16

The α-acetoxypeptide (5 mm), ethylmercaptan (5 mm), triethylamine (5 mm) and 25 ml of dimethylformamide are reacted as previously described. The resulting blocked peptide is treated with hydrobromic acid in acetic acid as described to give the hydrobromide of L-alanyl-2-(thioethyl)-D,L-glycine which is converted to the zwitterion by treatment with propylene oxide. The D,L-diastereomeric mixture is separated as described in Example 13.

L-Alanyl-2-(thiobutyl)-D,L-glycine is prepared using butyl mercaptan (5 mm). L-alanyl-2-(thiobenzyl)-D,L-glycine is prepared using benzylmercaptan (5 mm). L-Alanyl-2-(3-aminopropylthio)-D,L-glycine is prepared using N-carbobenzoxy-3-aminopropylmercaptan (5 mm).

EXAMPLE 17

A mixture of 4.28 g (10 mm) of N-carbobenzoxy-L-alanyl-D,L-2-acetoxyglycine benzyl ester, 0.94 g (10 mm) of phenol, 10 g of (10 mm) triethylamine and 35 ml of dimethylformamide was stirred at room temperature for 18 hours. The mixture was concentrated. The residue was dissolved in ethyl acetate, washed with water (3×100 ml), dried (MgSO$_4$) and evaporated to give impure L-alanyl-2-(phenoxy)-D,L-glycine as the ester derivative. Purification was obtained by using medium pressure chromatography over a silica gel column with an eluent of methylene chloride (300 ml) and 10% methanol-methylene chloride (1 l).

A mixture of 0.75 g (1.5 mm) of the D,L-isomeric mixture, purified as described in Example 13, was dissolved in 50 ml of methanol with heating and 0.4 g of 10% palladium-on-charcoal was added. The mixture was hydrogenated using a Parr hydrogenation apparatus for a total of 8.5 hours. The catalyst was filtered off. The filtrate was evaporated. The residue was dissolved in water, filtered and lyophylized to give 0.26 g (73%) of a diastereoisomeric mixture of L-alanyl-2-(phenoxy)-D,L-glycine.

High pressure liquid chromatography (HPLC), using a reverse phase modified silica gel $C_{18}$ column with an eluent of 100% water (300 ml), 10% methanol-water (1 l), 20% methanol-water (1 l), separated the L-L and the L-D isomers.

The L-L isomer had a rotation as follows: $[\alpha]_D^{25}$ (1, $H_2O$) = −61.8.

Anal. Calcd. for $C_{11}H_{14}N_2O_4 \cdot \tfrac{3}{4}H_2O$: C, 52.47; H, 5.96; N, 11.13. Found: C, 52.76; H, 5.77; N, 11.30.

The L-D isomer had a rotation as follows: $[\alpha]_D^{25}$ (1, $H_2O$) = +54.9.

Anal. Calcd. for $C_{11}H_{14}N_2O_4 \cdot \tfrac{3}{4}H_2O$: C, 52.47; H, 5.96; N, 11.13. Found: C, 52.72; H, 5.62; N, 11.10.

L-Alanyl-2-(2,4-dichlorophenoxy)-D,L-Glycine

As above using 2,4-dichlorophenol 15 mml.

L-Alanyl-2-[4-(2-aminoethyl)phenoxy]-D,L-Glycine

As above using 4-(N-carbobenzoxy-2-aminoethyl)phenol.

EXAMPLE 18

A mixture of 7.63 g (35.5 mm) alanine benzyl ester hydrochloride, 4.08 g (35.5 mm) of N-ethylmorpholine and 150 ml of dimethylformamide was cooled to 0°. To this mixture was added 10.5 g (35.5 mm) of N-carbobenzoxy-L-alanyl-D,L-2-hydroxyglycine, 4.79 g (35.5 mm) of hydroxybenzotriazole and 8.04 g (39.1 mm) of dicyclohexylcarbodiimide. The reaction mixture was stirred at 0° for 45 minutes and, then, for 15 hours at room temerature after which the crude reaction mixture was filtered and concentrated. The residue was dissolved in 500 ml of ethyl acetate, washed with dilute sodium bicarbonate solution (3×100 ml), 10% citric acid solution (3×100 ml), water (3×100 ml), saturated sodium chloride solution (3×100 ml) and dried ($MgSO_4$). Evaporation of the solvent produced a white solid which was recrystallized from an acetone-hexane mixture (2:1) to give 16.3 g (100%) of N-carbobenzoxy-L-alanyl-D,L-2-hydroxyglycyl-L-alanine benzyl ester.

A 1.0 g (2.19 mm) portion of N-carbobenzoxy-L-alanyl-D,L-2-hydroxyglycyl-1-alanine benzyl ester was treated with 25 ml of acetic anhydride and cooled to ~0° in an ice-water bath. Then, 25 ml of pyridine was added and the reaction mixture stored at 5° for 15 hours. The reaction mixture was concentrated. The resulting residue was triturated with a 1:1 ethyl ether-petroleum ether solution, filtered and dried to give 0.82 g (75%) of N-carbobenzoxy-L-alanyl-D,L-2-acetoxyglycyl-L-alanine benzyl ester (TLC 95:5 methylene chloride methanol, silica gel, $R_f$=0.64; $^1H$ and $^{13}C$ NMR consistent with structure.)

A mixture of 2.0 g (4.0 mm) of N-carbobenzoxy-L-alanyl-D,L-2-acetoxyglycyl-L-alanine benzyl ester, 3.5 g (12 mm) of trimethioprim and 50 ml of dimethylformamide was stirred for 1 hour. The mixture was concentrated. The residue was dissolved in 400 ml of ethyl acetate and washed with water (3×75 ml) and brine (75 ml), dried ($MgSO_4$), concentrated. The residue was flash chromatographed to give 1.95 g (67%) of a foamy solid, N-carbobenzoxy-L-alanyl-2-[[4-amino-5[(3,4,5-trimethoxyphenyl)methyl]pyrimidin-2-yl]-amino]D,L-glycyl-L-alanine benzyl ester, which was characterized by nuclear magnetic resonance (NMR) and mass spectral analysis.

A mixture of 0.76 g (1.04 mol) of the blocked peptide, 0.37 g of 10% palladium-on-charcoal and 100 ml of methanol was hydrogenated in a Parr apparatus at 50 psi for 14 hours. The catalyst was filtered off. The filtrate was concentrated, dissolved in water and lyophilized to give 0.48 g of L-alanyl-2-[[4-amino-5[(3,4,5-trimethoxyphenyl)methyl]-pyrimidine-2-yl]amino]D,L-glycyl-L-alanine. Rapid medium pressure chromatography gave the analytically pure mixture of diastereoisomers. Careful chromatography on the same mixture successfully separated the diastereomers.

The L,L,L isomer had a rotation as follows: $[\alpha]_D^{25}$ (1, $H_2O$) = −27.0.

Anal. Calcd. for $C_{22}H_{31}N_7O_7 \cdot 1\tfrac{3}{4}H_2O$: C, 49.20; H, 6.47; N, 18.25. Found: C, 49.10; H, 6.33; N, 18.16.

The LDL isomer had a rotation as follows: $[\alpha]_D^{25}$ (1, $H_2O$) = −58.0.

Anal. Calcd. for $C_{22}H_{31}N_7O_7 \cdot 2H_2O$: C, 48.79; H, 6.51; N, 18.10. Found: C, 48.54; H, 6.27; N, 18.24.

EXAMPLE 20

A mixture of 2.14 g (5.0 mm) of N-carbobenzoxy-L-alanyl-D,L-2-acetoxyglycine benzyl ester, 0.46 g (5.0 mmol) of aniline, 0.50 g (5.0 mm) of triethylamine and 50 ml of dimethylformamide was stirred at room temperature for 2 hours. The mixture was concentrated. The residue was dissolved in ethyl acetate and washed with water (3×50 ml) and brine (50 ml), dried ($MgSO_4$), concentrated and flash chromatographed over silica gel to give 2.46 g (100%) of N-carbobenzoxy-L-alanyl-2-(anilinyl)-D,L-glycine benzyl ester. Crystallization from hexane/acetone gave an analytically pure sample as a mixture of diastereomers.

A mixture of 0.81 g (1.75 mmol) of the blocked peptide prepared above, 0.4 g of 10% palladium-on-charcoal and 150 ml of methanol was hydrogenated in a parr apparatus at 50 psi for 8 hours. The catalyst was filtered. The filtrate was concentrated, dissolved in water and lyophilized to give 0.40 g of a mixture of diastereomeric L-alanyl-2-(anilino)-D,L-glycines.

A 200 mg portion of this material was separated into the purified diastereomers by medium pressure reverse phase chromatography as described above.

The L,L isomer had a rotation as follows: $[\alpha]_D^{25}$ (1, $H_2O$) = +70.0.

Anal. Calcd. for $C_{11}H_{15}N_3O_3 \cdot 1\tfrac{1}{2}H_2O$: C, 49.99; H, 6.86; N, 15.96. Found: C, 49.97; H, 6.51; N, 15.96.

The L,D isomer had a rotation as follows: $[\alpha]_D^{25}$ (1, $H_2O$) = +39.9.

Anal. Calcd. for $C_{11}H_{15}N_3O_3 \cdot 1\tfrac{1}{2}H_2O$: C, 49.99; H, 6.86; N, 15.96. Found: C, 49.93; H, 6.51; N, 16.06.

EXAMPLE 21

A 2.5 g (5.0 mmol) portion of N-carbobenzoxy-L-alanyl-α-acetoxyglycyl-L-alanine benzyl ester, 0.51 ml (0.55 g, 5.0 mmol) of thiophenol and 0.51 g (5 mmol) of triethylamine were combined in 50 ml of dimethyl formamide. Thin layer chromatography (TLC) (95:5 methylene chloride, methanol, silica plates) indicated the disappearance of acetate after 0.25 hours. After 30 minutes, the reaction was concentrated, dissolved in 200 ml of ethyl acetate and washed with 3×25 ml of water and 25 ml of brine, dried ($MgSO_4$) and concentrated to give 2.31 g of a light yellow foam, N-carbobenzoxy-L-alanyl-D,L-(α-S-phenyl)glycyl-L-alanine benzyl ester. TLC indicated minor impurities.

The material was flash chromatographed 1.5"×6" column of Baker flash silica gel, eluting with methylene chloride followed by 29% methanol in methylene chloride to give 2.25 g (82%) of pure product. $^1HNMR$ ($CDCl_3$) δ8.0–7.0 (m, 15), 6.2–58 (m, 2), 5.25 (S, 1), 5.15 (S, 1), 5.10 (S, 2), 4.8–4.2 (m, 3), 1.3 (t, 6); $^{13}C$ NMR ($CDCl_3$) δ172.2, 171.8, 166.9, 155.8, 136.3, 135.3, 134.8, 130.1, 128.8, 128.5, 128.3, 128.0, 127.8, 67.0, 66.7, 57.6, 50.4, 48.4, 18.9, 18.2, 18.0. H (CH$_2$Cl$_2$) 3420, 3040, 2990, 1740, 1660, 1500 cm$^{-1}$.

A 1.0 g (1.8 mmol) portion of the blocked diastereomeric mixture was added to 40 ml of hydrobromic acid saturated acetic acid at 20°. The reaction was stirred at room temperature for 6 hours. The volatiles were removed under vacuum. The resulting oil was triturated with ether, filtered, dissolved in 10 ml of ethanol and treated with an excess (3 ml) of propylene oxide, then, refrigerated for 16 hours.

The resulting solid was filtered, washed with acetone and dried to give 0.42 g (71%) of the zwitterion.

The diastereomeric mixture was injected onto a RP-18 MPLC column, which was described above, and eluted with a stepwise gradient of 0.5 L of water and 1 L of 20% methanol in water to elute the more mobile L-alanyl-L-(S-phenyl)-glycyl-L-alanine; 76 mg (18%) and, then, the less mobile D-isomer.

The L,L,L isomer had a rotation as follows: $[\alpha]_D^{25}$(1, H$_2$O)= +102.9.

Anal. Calcd. for C$_{14}$N$_{19}$N$_3$O$_4$S.1¼H$_2$O: C, 48.33; H, 6.23; N, 12.07. Found: C, 48.06; H, 5.81; N, 12.56.

The L,D,L isomer had a rotation as follows: $[\alpha]_D^{25}$(1, H$_2$O)= −150.6.

Anal. Calcd. for C$_{14}$H$_{19}$N$_3$O$_3$S.1⅛H$_2$O: C, 48.64; H, 6.20; N, 12.15. Found: C, 48.08; H, 5.84; N, 12.72.

EXAMPLE 22

A mixture of 0.428 g (1.0 mmol) of N-carbobenzoxy-L-alanyl-D,L-2-acetoxyglycine benzyl ester, 0.265 g (1.0 mmol) of albendazole, 0.101 g (5.0 mmol) of triethylamine and 10 ml of dimethylformamide was stirred at room temperature for 6 hours. The resulting solution was concentrated. The residue was dissolved in ethyl acetate, washed with water (3×50 ml) and brine (50 ml), dried (MgSO$_4$), concentrated and redissolved in methylene chloride. A minor amount of insoluble material was filtered off and the filtrate was flash chromatographed (MPLC) over silica gel to give 0.25 g (40%) of a white foamy solid. Spectroscopic analysis ($^1$N and $^{14}$C nmr, ir) was consistant with a mixture of isomers of N-carbobenzoxy-L-alanyl-2-(albendazole)-D,L-glycine benzyl ester. HPLC also indicated a mixture.

A 0.80 g (1.26 mmol) portion of blocked peptide mixture was added to 50 ml of acetic acid saturated with hydrobromic acid and then stirred at room temperature for 6 hours. The reaction was poured into 1 L of ether, filtered and dried under vacuum. The resulting solid HBr salt was dissolved in 20 ml of absolute ethanol and combined with 2 ml of propylene oxide. The white solid which formed on slow cooling to −4° was filtered off and dried under vacuum to give 0.217 g (53%) of L-alanyl-2-(albendazole)-D,L-glycine.

Anal. Calcd. for C$_{17}$H$_{23}$N$_5$O$_5$S.½H$_2$O: C, 48.79; H, 5.78; N, 16.73. Found: C, 48.46; H, 5.54; N, 16.22.

This compound was found to have antiparasitic activity comparable to, or greater than, albendazole against Fasciola hepatica and Nematospiroides dubius infections in mice given subcutaneously at 15 mg/kg for eight days. In an in vitro screen against Caenorhabditis elegans, nematostatic activity was demonstrated at concentrations of 10 and 100 μg/ml.

EXAMPLE 23

A 1.68 g (20 mmol) portion of sodium bicarbonate in 120 ml of 1:1 tetrahydrofuran-water was deoxygenated with a stream of argon gas. Aminopropylthiol hydrochloride (1.27 g, 10 mmol) was added followed by 2.35 g (10.8 mmol) of di-t-boc carbonate. The mixture was heated at reflux for 2 hours maintaining argon flow. The cooled mixture was neutralized to pH 7 and concentrated. The aqueous phase was acidified to pH 2 and extracted with 2×75 ml portions of ethyl acetate. The combined extracts were washed with 1.5 N hydrochloric acid and brine. The dried and washed extract was concentrated to an oil which was pumped under a high vacuum overnight. A total of 1.8 g of material which was largely the t-boc derivative by thin layer analysis (95:5 methylene chloride-methanol).

The crude sample was purified by flash chromatography to give 1.61 g of pure N-t-boc-3-aminopropylthiol.

A mixture of 0.428 g (1.0 mmol) of the 2-acetoxy starting material prepared as described in Example 1, 0.191 g (1.0 mmol) of the t-boc prepared above, 0.1 g (1 mmol) of triethylamine and 1.0 ml of dimethylformamide was stirred for 12 hours. The mixture was concentrated and partitioned between 25 ml of water and 2×35 ml of ethyl acetate. The organic extract was washed with water and brine, dried and concentrated to give 0.66 g of the α-thiol t-boc product. The product was flash chromatographed, then, further purified by medium pressure liquid chromatography using 1% methanol in methylene chloride to give 0.443 g (80%) of pure product. H$^1$- and C$^{13}$-Nuclear magnetic resonance spectra were good.

The t-boc (0.10 g) and 10 ml of trifluoroacetic acid were allowed to stand at room temperature for 5 minutes. The excess acid was evaporated and the residue triturated three times with ether. The ether was dried and concentrated to give crystals of N-carbobenzoxy-L-alanyl-D,L-2-(3-aminopropylthio)-glycine, benzyl ester as the trifluoro acetic acid salt.

Anal. Calc'd for C$_{25}$H$_{30}$F$_3$N$_3$O$_7$.1.5H$_2$O: C, 52.39; H, 5.36; N, 7.20. Found: C, 52.84; H, 5.85; N, 7.39.

This product exhibits the biological properties of a lysine-mimetic dipeptide. When exposed to biological fluid containing trypsin, the benzyl ester is cleaved, then, carboxypeptidase B splits the peptide bond releasing -S(CH$_2$)$_3$NH$_2$ which is detected using Ellman's reagent as described hereinafter.

The homologous compound, N-carbobenzoxy-L-alanyl-D,L-2-(2-aminoethylthio)-glycine, benzyl ether is prepared using aminoethylthiol as starting material in the process described above. Using 3-N-tosylguanidinopropylthiol, prepared as known to the art, gives N-carbobenzoxy-L-alanyl-D,L-α-3-(N-tosylguanidinopropylthio)-glycine, benzyl ether which as an arginine-mimetic is useful as a chromogenic detector of thrombin or thrombin derivatives in biological samples.

EXAMPLE 24

Substituting a stoichiomeric quantity of N-carbobenzoxy-L-phenylglycylamide, N-carbobenzoxy-L-phenylalanylamide or N,N-bisd-carbobenzoxy-L-lysylamide in the reactions of Examples 1 and 2 gives N-carbobenzoxy-L-phenylglycyl-2-hydroxy-D,L-glycine, N-carbobenzoxy-L-phenylalanyl-2-hydroxy-D,L-glycine and N,N-biscarbobenzoxy-L-lysyl-2-hydroxy-D,L-glycine.

N-carbobenzoxy-L-phenylglycyl-2-hydroxy-D,L-glycine is reacted with a stoichiometric quantity of benzoyl chloride in pyridine to give the 2-benzoyloxy compound which is treated with 5-fluorouracil and deblocked using palladium-on-charcoal and cyclohexene as described in Example 2 to give L-phenylglycyl-2-(5-fluorouracil-1-yl)-D,L-glycine.

N-carbobenzoxy-L-phenylalanyl-2-hydroxy-DL-glycine is reacted with ethylchloroformate in pyridine to give the 2-ethylformate which is reacted with 5-fluorouracil and deblocked to give L-phenylalanyl-2-(5-fluorouracil-2-yl)-D,L-glycine.

N,N-biscarbobenzoxy-L-lysyl-2-hydroxy-D,L-glycine is acylated with acetyl chloride and pyridine, reacted with 5-fluorouracil and deblocked as described in Example 2 to give L-lysyl-2-(5-fluorouracil-2-yl)-D,L-glycine.

EXAMPLE 25

Substituting N-carbobenzoxyleucine for N-carbobenzoxyalanine in Example 5 gives D,L-leucyl-L-alanyl-2-(5-fluorouracil-1-yl)-D,L-glycine. Substituting N-carbobenzoxy-D,L-phenyl alanine gives D,L-phenylalanyl-L-alanyl-2-(5-fluorouracil-1-yl)-D,L-glycine. Substituting N-carbobenzoxy-D,L-alanyl-D,L-leucyl gives D,L-alanyl-D,L-leucyl-L-alanyl-2-(5-fluorouracil-1-yl)-D,L-glycine. Substituting N-carbobenzoxy-alanyl-alanyl-alanyl gives alanyl-alanyl-alanyl-L-alanyl-2-(5-fluorouracil-1-yl)-D,L-glycine.

Using either other amino acids or oligopeptides of the art, such as those described in one of the volumes of "Synthetic Peptides", of reference above, or other biologically useful warheads (W), other compounds of this invention are prepared.

EXAMPLE 26

A mixture of 5 g (0.0266 m) of tert.-butoxycarbonyl alanyl amide, 3.9 g (0.03 m) of tert.-butyl glyoxylate, prepared by oxidation of tert.-butyl tartrate, and 100 ml of benzene is heated at reflux using azeotropic conditions for 54 hours to complete the reaction to give N-tert.-butoxycarbonyl-L-alanyl-2-hydroxy-D,L-glycine, tert.-butyl ester which is used as above with appropriate removal of the t.-boc groups such as reacting with trifluoroacetic acid.

Antimicrobial Examples

A prototypal compound, L-alanyl-2-(5-fluorouracil-2-yl)-L-glycine, was evaluated against representative fungal and bacterial organisms.

Methods of Testing

A. Fungi (Disk diffusion method):

*Candida albicans* strains B-311 and BC 759, obtained from Smith Kline and French Laboratory Culture Collection were grown in a trypticase soy broth at 28° for 7 hours. The seeded plates, with this medium containing 1.5% agar, were prepared by inoculating 1 ml of the inoculum in 1 l. of yeast-carbon base medium, containing 200 µg/ml of lysine or glutamate as a sole source of nitrogen.

B. Fungi [Minimum inhibitory contraction (MIC)]:

The minimum inhibitory concentration of the test compound was determined by two-fold broth dilution tests in yeast carbon base medium, containing 200 µg/ml of sodium glutamate. The compounds were diluted from 280 µg/ml to 0.25 µg/ml and the test medium was inoculated with a suspension of *C. albicans* grown in the same medium for 15 hours at 37°. The final inoculum sizes in the tests we approximately $10^4$ cfu/ml and $10^3$ cfu/ml. The tubes were incubated at 37° for 24 and 48 hours and observed for inhibition.

C. Bacteria (Disk diffusion method):

A method similar to A above but using *E. coli* was used which employs a M-9 medium (basic salts with ammonium ion as the nitrogen source and glucose as the carbon source).

Results of Testing (1) *C. albicans* in Method A:

| L-alanyl-2-(5-fluorouracil-1-yl)-L-glycine | | L-alanyl-2-(5-fluorouracil-1-yl)-D-glycine | |
|---|---|---|---|
| µg/ml | zone size (mm) | µg/ml | zone size (mm) |
| 1000 | 30 | 1000 | 0 |
| 500 | 26 | 500 | 0 |
| 250 | 22 | 250 | 0 |
| 125 | 20 | 125 | 0 |
| 62 | 16 | 62 | 0 |

These data demonstrate the unique contribution of the L-L configuration in the compounds of this invention.

(2) *C. albicans* in Method B:

| | Alanyl-2-(5-fluorouracil-2-yl)-glycine MIC (µg/ml) | | | |
|---|---|---|---|---|
| Strains | 5-FU | L-DL | L-L | L-D | Amphotericin B |
| BC 759 | 1.0 | 6.3 | 1.6 | >100 | 1.25 |
| B 311 | 4.0 | 25 | 12.5 | >100 | 1.25 |
| 3153A | 1.0 | 25 | 12.5 | >100 | 1.25 |

These data indicate antifungal activity for the L- DL and, especially, the L-L-diastereoisomers but none for the L-D isomer.

(3) *E. coli* M. 2626 in Method C:

| | Zone size (mm) | | | |
|---|---|---|---|---|
| conc. (µg/disk) | 5-fluorouracil (FU) | FU + 2-FU-alanyl-L-glycine | FU + alanyl-alanine | 2-FU-L-alanyl-L-glycine + alanyl-alanine |
| 25.0 | 46 | 31 | — | — |
| 12.5 | 41 | 26 | 41 | 0 |
| 6.0 | 40 | 27 | 40 | 0 |
| 3.0 | 38 | 25 | 38 | 0 |
| 1.5 | 33 | 22 | 33 | 0 |

These data show activity is due to prodrug itself, not to its pre-dissociated parts.

(4) *C. albicans* B-310 in Test B:

| MIC (µg/ml, 24 hours | |
|---|---|
| L-alanyl-2-(5-fluorouracil-2-yl)-L-glycine | L-alanyl-2(5-fluorouracil-2-yl)-D-glycine |
| 12.5 | >200 |

(5) *C. albicans* B-311 in Test A:

| Alanyl-2-(5-fluorouracil-2-yl)-glycine | | | | |
|---|---|---|---|---|
| Conc. (µg/desk) | 5-Fu | L-DL | L-L | L,D |
| 25 | 44 | 20 | 30 | 0 |
| 12.5 | 40 | 20 | 26 | 0 |
| 6.0 | 30 | 20 | 22 | 0 |
| 3.0 | 30 | 18 | 20 | 0 |
| 1.5 | 22 | 12 | 16 | 0 |

These data confirm the activity of the isomer with a L-configuration in the terminal glycine unit of the oligopeptide chain.

(6) Stability of α-substituted Glycine Peptides to Aqueous Solutions and Enzyme Catalyzed Warhead Release:

The α-substituted glycine peptide of Example 4, having a structure which contains a sulfhydryl group linked at the α-position of glycine, was found to be stable (t ½ ~5000 min) in 0.2 M phosphate buffer (pH 7.0). Upon addition of the enzyme, Leucine Aminopeptidase, the warhead was released. The release was maintained at a linear rate over the observation period (5 min). This observation was repeated at pH 7.5, at which pH there was, again, no noticeable increase in the non-enzymatic warhead release; however, the enzymatically catalyzed release again proceeded at twice the previous rate. This observation is consistent with literature reports of the optimal pH necessary for the efficacy of this enzyme. Similar results were obtained with the product of Example 21.

The procedure described here is applied to any enzyme which is capable of hydrolyzing the stabilizing peptide bond, such as that between units 1 and 2 of the enzyme substrates of formula 1, for example, enzymes such as carboxypeptidase A or trypsin or the various serum proteases. The procedure described here is a more verstile detection system than those used in the prior art which use chromogenic peptide substrates such as leucine p-nitroanilide.

These observations were obtained by colorimetric assay, which involves the reaction between a free sulfhydryl group and 5,5'-dithio-bis(2-nitrobenzoic acid), the Ellman reagent, to produce a yellow color as follows:

Reaction Sequence B

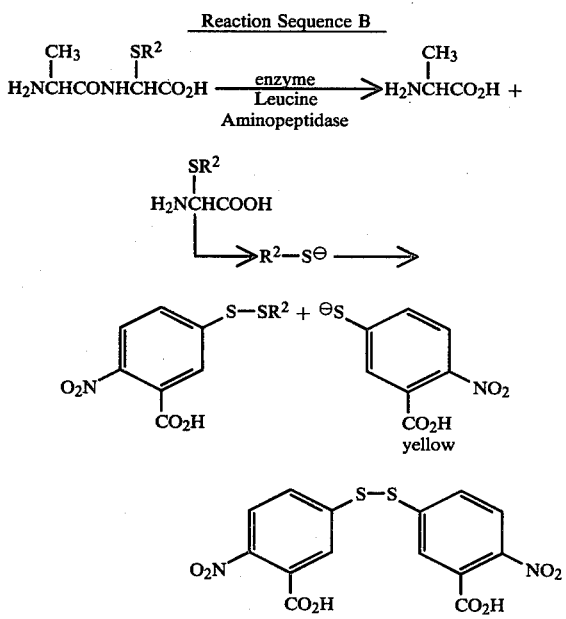

Assay

The peptide from Example 4 was dissolved in 4 mM of phosphate buffer solution (pH 7) containing in Ellman reagent at a level of 4 mg/ml to produce a 1 mM solution of the peptide. The resulting mixture was monitored using a spectrophotometer at a wavelength of 412 nm. To 1 ml of this solution was added 100 μg of hog kidney leucine aminopeptidase (Sigma) and the enzymatic hydrolysis was continuously monitored at 412 nm.

| Data | Phosphates buffer λ(412) |
|---|---|
| Time (sec) | |
| 0 | 0.090 |
| 1 | 0.093 |
| 2 | 0.095 |
| enzyme added: | |
| 3 | 0.109 |
| 4 | 0.127 |
| 5 | 0.142 |
| 6 | 0.161 |
| 7 | 0.180 |
| 8 | 0.199 |

Reaction mixture contained 1 mM peptide, Ellman's reagent 4 mg/ml, phosphate buffer 4 mM (pH 7).

| | p moles per min |
|---|---|
| Spontaneous Rate | 65 |
| plus 100 μg enzyme | 504 |

What is claimed is:

1. A compound of the structural formula:

in which:

R$^1$ is a C$_{1-4}$ lower alkyl, phenyl, ω-amino-C$_{2-4}$-alkyl or benzyl;

P is H, carbobenzoxy or from 1–4 D- or L-residue units selected from the group consisting of glycyl, phenylglycyl, alanyl, phenylalanyl, lysyl, ornithyl, norvalyl, valyl, norleucyl, isoleucyl or leucyl, either in the natural L- or in the D-configuration; and Q is hydroxy, benzyloxy or from 1–4 residue units of an amino acid such as glycyl, phenylglycyl, alanyl, phenylalanyl, lysyl, ornithyl, norvalyl, valyl, norleucyl, isoleucyl or leucyl, either in the natural L- or in the D-configuration; and W is a residue of a nucleophilic, pharmaceutically useful antimicrobial or antiparasitic agent, which agent residue is reversibly substituted and is released by protease degradation, said compound having an L or D,L configuration at both the W-substituted glycyl unit and the R$^1$ containing unit, or its pharmaceutically acceptable salts; or other ester derivatives.

2. The compound of claim 1 in which the configurations of the amino acids are all L.

3. The compound of claim 2 in which P is hydrogen and Q is hydroxy.

4. The compound of claim 2 in which P is H, R$^1$ is methyl and Q is hydroxy.

5. The compound of claim 1 in which P is L-alanyl, R$^1$ is methyl, Q is OH and W is an antimicrobial compound.

6. The compound of claim 5 in which P is hydrogen, Q is hydroxy, R$^1$ is methyl and W is 5-fluorouracil-2-yl.

7. The compound of claim 1 in which P is hydrogen, Q is hydroxy, $R^1$ is methyl and W is a benzimidazole anthelmintic.

8. The compound of claim 1 in which P is hydrogen, Q is hydroxy, $R^1$ is methyl and W is $C_{1-4}$-alkylthio or

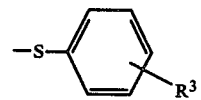

in which $R^3$ is H or 1 or 2 substituents of the group comprising $C_{1-4}$ alkyl, $C_{1-4}$ alkoxy, cyano, halo or $C_{1-4}$ alkylthio.

9. The compound of claim 1 in which $R^1$ is methyl, P is carbobenzoxy, Q is benzyloxy and W is ω-aminopropylthio.

10. The compound of claim 8 in which W is phenylthio, being L-alanyl-L-(α-phenylthio)glycine.

* * * * *